US009588052B2

(12) United States Patent
Landgrebe et al.

(10) Patent No.: US 9,588,052 B2
(45) Date of Patent: Mar. 7, 2017

(54) WATER-BASED ORGANIC BISMUTH, ELEMENTAL SULFUR AND LITHIUM CARBONATE STERILIZATION INDICATOR COMPOSITION

(71) Applicant: 3M INNOVATIVE PROPERTIES COMPANY, St. Paul, MN (US)

(72) Inventors: Kevin D. Landgrebe, Woodbury, MN (US); Ranjani V. Parthasarathy, Woodbury, MN (US); Anthony E. Bennett, Maplewood, MN (US); Peter T. Elliott, Woodbury, MN (US); Steven S. Kirckof, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 115 days.

(21) Appl. No.: 14/366,731

(22) PCT Filed: Dec. 18, 2012

(86) PCT No.: PCT/US2012/070326
§ 371 (c)(1),
(2) Date: Jun. 19, 2014

(87) PCT Pub. No.: WO2013/096299
PCT Pub. Date: Jun. 27, 2013

(65) Prior Publication Data
US 2014/0370604 A1 Dec. 18, 2014

Related U.S. Application Data

(60) Provisional application No. 61/578,067, filed on Dec. 20, 2011.

(51) Int. Cl.
*G01N 21/78* (2006.01)
*C09D 11/50* (2014.01)
*G01N 31/22* (2006.01)
*B05D 3/02* (2006.01)

(52) U.S. Cl.
CPC .......... *G01N 21/78* (2013.01); *B05D 3/0272* (2013.01); *C09D 11/50* (2013.01); *G01N 31/226* (2013.01)

(58) Field of Classification Search
CPC ...................................... G01N 21/78
USPC ..................................... 436/1, 166
See application file for complete search history.

(56) References Cited

U.S. PATENT DOCUMENTS 2,118,144 A * 5/1938 Berman ............... G01K 11/12
106/31.64
3,360,338 A 12/1967 Edenbaum
3,386,807 A * 6/1968 Edenbaum ............... A61L 2/28
374/106
3,471,422 A 10/1969 Edlein
3,684,737 A * 8/1972 Emigh ..................... A61L 2/28
116/207
4,298,569 A * 11/1981 Read ..................... G01N 31/226
116/206
5,057,433 A * 10/1991 Douglas .................. A61L 2/28
422/119
5,916,816 A 6/1999 Read
5,990,199 A * 11/1999 Bealing .................... A61L 2/28
106/31.13
9,170,245 B2 * 10/2015 Landgrebe ............... A61L 2/28
9,176,103 B2 * 11/2015 Whitman ............. G01N 31/226
2003/0211618 A1 * 11/2003 Patel ....................... A61L 2/07
436/38
2011/0312096 A1 12/2011 Whitman

FOREIGN PATENT DOCUMENTS

| JP | 53-4604 | * | 1/1978 |
|---|---|---|---|
| JP | 2-211162 | | 8/1990 |
| JP | 4-62746 | | 10/1992 |
| JP | 4-364174 | | 12/1992 |
| JP | 2002-48715 | | 2/2002 |
| JP | 2002-322315 | * | 11/2002 |
| JP | 2002-323451 | * | 11/2002 |
| JP | 2004-317433 | * | 11/2004 |
| JP | 2005-178871 | * | 7/2005 |
| JP | 2005-329983 | * | 12/2005 |
| JP | 2006-1206 | * | 1/2006 |
| JP | 2006-3274 | * | 1/2006 |
| JP | 2006-104346 | * | 4/2006 |
| JP | 2010-71883 | | 4/2010 |
| WO | WO 2010-078422 | | 7/2010 |

OTHER PUBLICATIONS

Duncan, W., "Bismuth Citrate and Liquor Bismuthi" in Yearbook of Pharmacy, Braithwaite, J. O. editor, J. & A. Churchill, London, 1902, 476-482.*
"Bismuth citrate" Chemical Book downloaded from http://www.chemicalbook.com/ProductMSDSDtailCB8272731_EN.htm May 4, 2016, 3 pages.*
"Bismuth citrate" ChemSpider downloaded from http://www.chemspider.com/Chemical-Structure.12583.html May 4, 2016, 3 pages.*
"Bismuth citrate" Science Lab downloaded from http://www.sciencelab.com/msds.php?msdsld=9923100 May 4, 2016, 5 pages.*
Physical Constants of Inorganic Compounds downloaded from https://www.slac.stanford.edu/BFROOT/www/Detector/Backgrounds/BkG4Sim/Planning/Validations/neutronCounters/04_02_85.pdf May 4, 2016, 60 pages.*
Fairbrother, F. et al, Journal of Polymer Science 1955, 16, 459-469.*
Hartler, N. et al, Industrial & Engineering Chemistry Process Design and Development 1967, 6, 398-406.*
International Search Report for PCT International Application No. PCT/US2012/070326 mailed Apr. 11, 2013, 4 pages.

* cited by examiner

Primary Examiner — Arlen Soderquist

(57) ABSTRACT

Water-based formulations comprising an indicating composition dispersed in water are described. The water-based indicating compositions include an organic Bi(III) compound, a sulfur source, and a carbonate salt. Formulations further including a resin and/or an acidic additive are also described.

11 Claims, No Drawings

WATER-BASED ORGANIC BISMUTH, ELEMENTAL SULFUR AND LITHIUM CARBONATE STERILIZATION INDICATOR COMPOSITION

CROSS REFERENCE TO RELATED APPLICATIONS

This application is a national stage filing under 35 U.S.C. 371 of PCT/US2012/070326, filed Dec. 18, 2012, which claims priority to U.S. Application No. 61/578,067, filed Dec. 20, 2011, the disclosure of which is incorporated by reference in its/their entirety herein.

FIELD

The present disclosure relates to water-based compositions containing organic Bi(III) compounds, carbonate salts, and a sulfur source. The use of such compositions to form steam sterilization indicators is also described.

SUMMARY

Briefly, in one aspect, the present disclosure provides an indicator formulation comprising an indicating composition dispersed in water. The indicating composition comprises an organic Bi(III) compound; a sulfur source; and a carbonate salt. The organic Bi(III) compound and the sulfur source are selected such that at least one of the organic Bi(III) compound and the sulfur source has solubility in water at 20° C. of less than 5 grams/100 ml. In some embodiments, both the organic Bi(III) compound and the sulfur source have solubility in water at 20° C. of less than 5 grams/100 ml.

In some embodiments, the composition comprises bismuth subcarbonate formed in situ. In some embodiments, the organic Bi(III) is selected from the group consisting of bismuth subsalicylate, bismuth citrate, bismuth tartrate, and combinations thereof. In some embodiments, the sulfur source is selected from the group consisting of sulfur, 1,3-diphenylthiourea, sodium thiosulfate, and combinations thereof. In some embodiments, the carbonate salt is selected from the group consisting of lithium carbonate, magnesium carbonate, sodium carbonate, sodium bicarbonate, and combinations thereof.

In some embodiments, the formulation further comprises an acidic compound, e.g., citric acid, gallic acid, oxalic acid, and combinations thereof.

In some embodiments, the formulation further comprises a resin, e.g., an acrylic resin.

In another aspect, the present disclosure provides an indicator tape comprising a substrate and an indicator composition on a portion of at least one surface of the substrate. The indicator tape is prepared by the process of applying an indicator formulation of the present disclosure to the surface of the substrate and drying the formulation.

The above summary of the present disclosure is not intended to describe each embodiment of the present invention. The details of one or more embodiments of the invention are also set forth in the description below. Other features, objects, and advantages of the invention will be apparent from the description and from the claims.

DETAILED DESCRIPTION

A variety of products and articles, including, for example, medical instruments, devices, and equipment, must be sterilized prior to use to prevent bio-contamination of a wound site, a sample, an organism, or the like. A number of sterilization processes are used that involve contacting the product or article with a sterilant. Examples of such sterilants include steam, ethylene oxide, hydrogen peroxide, and the like. Steam sterilization is widely used, at least in part because multiple batches of articles can be subjected to sterilization conditions during a 24 hour period using a single steam sterilizer.

Monitoring for conditions sufficient for steam sterilization is generally carried out by placing an appropriate sterilization indicator along with the product and/or article to be sterilized within a sterilization chamber. A variety of sterilization indicators, including chemical and biological indicators, are known and used for this purpose. Chemical indicators offer an advantage in that they can be read immediately at the end of a sterilization process. For example, internal chemical indicators are placed within an instrument tray prior to steam exposure. These indicators are read in the operating room upon opening the steam-exposed tray, prior to instrument removal. Process indicators such as labels and autoclave tapes have been used to indicate that a wrapped instrument tray or other wrapped article or articles have been exposed to steam.

Internal chemical indicators and process indicators, such as autoclave tapes, should indicate by color change their exposure to steam under various operating conditions associated with a level of exposure to steam adequate to achieve sterilization. However, these indicators should remain their original color, or near their original color, under other conditions in which the exposure to steam is inadequate for sterilization. For example, an autoclave tape should show a significant color change when subjected to steam in a hospital autoclave at 132-134° C. for around 3 or 4 minutes, and at 121° C. for around 20 minutes. Additionally, when tested using a steam resistometer according to ISO Standard 11140, an autoclave tape should show a significant color change on contact with steam at 134° C. for 2 minutes, and at 121° C. for 10 minutes, but should not show a significant color change on exposure to steam at 134° C. for 30 seconds nor at 121° C. for 3 minutes. Finally, an autoclave tape should not show a significant color change on exposure to dry heat at 140° C. for 30 minutes.

Steam sterilization indicator compositions for both internal indicators and process indicators that have been used include a polyvalent metal compound such as lead carbonate, and sulfur. Such indicators turn to brown or black when their color is fully developed by a steam sterilization condition. Because of environmental concerns, lead compounds have been and continue to be replaced by other polyvalent metal compounds. For example, U.S. Pat. No. 3,471,422 (Edbohm et al.) describes a time-temperature responsive color changing indicator composition based on a compound of a polyvalent metal and a sulfur material. The polyvalent metal is lead, copper, cobalt, nickel, bismuth, or cadmium. Also, Japanese Patent Kokai No. 4[1992]-364,174 (Takemura et al.) and Japanese Patent Kokai No. 4[1992]-62,746

(Koybayashi et al.) describe bismuth compounds that can be combined with sulfur or sulfur compounds such as thioureas to produce indicator compositions for steam sterilization. However, such compositions do not reliably turn black or even dark brown, and/or they take too long to turn black or dark brown under sterilization conditions of high temperature and humidity, or when exposed to dry heat they undergo a color change that is not markedly different from the color formed when the same composition is exposed to steam.

U.S. Pat. No. 5,916,816 (Read) describes solvent-based steam sterilization indicator compositions using bismuth oxychloride or bismuth subcarbonate, a sulfur source, and a compound capable of generating alkaline conditions when exposed to steam (e.g., carbonate salts). U.S. patent application Ser. No. 13/161,079 ("Chemical Indicator Compositions, Indicators and Methods," filed Jun. 15, 2011) also describes solvent-based steam sterilization indicator compositions comprising a bismuth oxide or an organic bismuth compound, a sulfur source, and a compound which makes the composition alkaline when exposed to water vapor at an elevated temperature (e.g., a carbonate salt).

Despite these advances, there is a continuing need for lead-free chemical indicators that can indicate that a steam sterilization process condition has been met. In particular, water-based compositions suitable for forming such indicators are desired.

Generally, lead-free chemical indicators are useful as steam-sterilization indicators, including autoclave tapes. Generally, acceptable chemical indicators will provide a distinct color change upon exposure to steam at conditions associated with acceptable sterilization conditions, with distinctly less color change when exposed to dry heat and/or steam at conditions associated with incomplete sterilization. Generally, steam sterilization is associated with conditions wherein steam condenses. As acceptable chemical indicator compositions are designed to turn color upon exposure to the steam and/or condensing water, it was believed that the chemical indicator formulations could not be prepared from water-based solutions; as such solutions would be expected to turn color during their preparation in water. Surprisingly, the present inventors discovered that water-based chemical indicator compositions could be prepared and used to produce effective steam-sterilization indicators.

Generally, the indicator formulations of the present disclosure include an indicating composition dispersed in water. The indicating composition comprises an organic Bi(III) compound; a sulfur source; and a carbonate salt. At least one of the organic Bi(III) compound and the sulfur source has solubility in water at 20° C. of less than 5 grams/100 ml.

Although inorganic Bi(III) compounds have been found suitable for use in the solvent-based compositions of the prior art, the present inventors determined that organic Bi(III) should be used in the preparation of the water-based indicator compositions of the present disclosure. Suitable organic Bi(III) compounds include bismuth subsalicylate (CAS Reg. No. 14882-18-9), bismuth gallate (3,4,5-trihydroxybenzoic acid bismuth salt, CAS Reg. No. 57206-57-2), bismuth subgallate (2,7-dihydroxy-1,3,2-benzodioxabismol-5-carboxylic acid, CAS Reg. No. 99-26-3), bismuth pyrogallate (1,2,3-benzenetriol, bismuth salt, basic, CAS Reg. No. 12001-49-9), bismuth acetate (bismuth triacetate, CAS Reg. No. 22306-37-2), bismuth citrate (CAS Reg. No. 110230-89-2), bismuth potassium citrate (CAS Reg. No. 57644-54-9), ammonium bismuth citrate (CAS Reg. No. 67953-07-5), bismuth lactate (CAS Reg. No. 6591-53-3), bismuth oxalate (CAS Reg. No. 6591-55-5), bismuth benzoate, bismuth formate, bismuth propionate, bismuth butyrate, bismuth pivalate (bismuth salt of 2,2-dimethylpropanoic acid), 2-propylpentanoic acid bismuth salt (CAS Reg. No. 94071-09-7), bismuth ascorbate, bismuth diethyldithiocarbamate (tris(diethyldithiocarbamato)bismuth (III), CAS Reg. No. 20673-31-8), bismuth dimethyldithiocarbamate, bismuth 2-ethylhexanoate (CAS Reg. No. 67874-71-9), bismuth neodecanoate (CAS Reg. No. 34364-26-6), bismuth oleate, bismuth gluconate, bismuth potassium D-gluconate, bismuth naphtholate (CAS Reg. No. 8039-60-9), naphthenic acid bismuth salt (CAS Reg. No. 85736-59-0), bismuth triglycollamate, bismuth sodium triglycollamate (N,N-bis(carboxymethyl)glycine disodium salt/N-(carboxymethyl)-N-[2-oxo-2-{(oxobismuthino)oxy}ethyl]glycine monosodium salt (3:1), CAS Reg. No. 5798-43-6), bismuth succinate (CAS Reg. No. 139-16-2), bismuth maleate (CAS Reg. No. 88210-84-8), bismuth tartrate (CAS Reg. No. 6591-56-6), bismuth sodium tartrate (CAS Reg. No. 31586-77-3), bismuth potassium tartrate (CAS Reg. No. 5798-41-4), bismuth tannate, 3-camphocarboxylic acid bismuth salt (CAS Reg. No. 4154-53-4), bismuth ethylcamphorate (CAS Reg. No. 52951-37-8), bismuth oxyquinoline (CAS Reg. No. 1300-75-0), 2-oxo-3-bornanecarboxylic acid bismuth salt (CAS Reg. No. 19495-28-4), bismuth valproate, and a combination thereof. Any of the compounds having at least one chiral center includes any one of the stereoisomers or any combination thereof, including racemic mixtures. For example, bismuth gluconate includes all forms of the gluconate (e.g., D-gluconic acid bismuth (III) salt (CAS Reg. No. 94232-39-0), L-gluconic acid bismuth (III) salt, and/or a racemic mixture thereof. For certain of these embodiments, the bismuth (III) compound is selected from the group consisting of bismuth subsalicylate, bismuth citrate, bismuth tartrate, and combinations thereof. For certain of these embodiments, the bismuth (III) compound is bismuth subsalicylate.

Although numerous compounds have been identified as suitable "compounds which make the composition alkaline when exposed to water vapor at an elevated temperature," the present inventors determined that carbonate salts should be used in the water-based compositions of the present disclosure. Suitable carbonate salts include lithium carbonate, potassium carbonate, magnesium carbonate, and sodium carbonate. In some embodiments, bicarbonate salts, including sodium bicarbonate, may be suitable.

As discussed in greater detail in the Examples section of the present disclosure, the present inventors discovered that the combination of an organic Bi(III) compound with a carbonate salt in water can result in the in situ formation of bismuth subcarbonate. Although the direct addition of bismuth subcarbonate to water failed to form an acceptable chemical indicator, the in situ formation of bismuth subcarbonate from the reaction of an organic Bi(III) compound and a carbonate salt led to good indicating compositions.

A wide variety of sulfur sources may be used in the water-based formulations of the present disclosure. Suitable sulfur sources include elemental sulfur, which is known to exist as an eight-membered ring of sulfur atoms. Under certain alkaline conditions, for example, in the presence of a nucleophile, such as hydroxide ion, the ring of sulfur atoms can be opened and sulfide ions can be formed from the resulting chain of sulfur atoms. In the presence of the sulfide ions, the bismuth compound can form bismuth sulfide, which is dark in color.

Other exemplary sulfur sources include disulfides; thioureas, such as N,N-diphenylthiourea; and thiocarbamates, as well as dithiocarbamates. Additionally, sulfide salts, such as zinc sulfide, calcium sulfide, potassium sulfide can be used as the sulfur source for certain embodiments.

Although a variety of both organic Bi(III) compounds and sulfur sources may be used, the present inventors determined that these materials should be selected such that at least one of the organic Bi(III) compound or the sulfur source be relatively insoluble in water. For example, at least one of the organic Bi(III) compound or the sulfur source should have solubility in water at 20° C. of less than 5 g/100 ml, e.g., less than 2 g/100 ml, less than 1 g/100 ml, or even less than 0.5 g/100 ml. Generally, the solubility can be determined through any of a variety of known procedures, and the solubility of many compounds is readily available in a variety of commonly available reference materials. As used herein, materials identified in a reference source as "insoluble" or "slightly soluble" are considered to have a solubility of less than 0.5 g/100 ml consistent with the meaning of such phrases to one of ordinary skill in the art.

In some embodiments, the compositions further comprise a resin, also referred to as a binder. Generally, the binder holds the composition in place when coated on a substrate. Preferably the binder comprises a film-forming material, which is stable to heat and water vapor. A film formed by the binder is sufficiently permeable to water vapor and steam to allow a desired color change to occur under sterilization conditions. Materials that the binder may comprise include, for example, styrene, acrylonitrile, acrylate and methacrylate polymers and copolymers (e.g., poly(methylmethacrylate) and methyl/n-butyl methacrylate copolymer), poly(vinyl acetate) and poly(vinylchloride) and copolymers thereof, and various derivatives of cellulose, including, for example, ethylcellulose and nitrocellulose. In certain embodiments, the binder may be an ultraviolet light-, visible light-, or thermally-curable material.

In some embodiments, the compositions of the present disclosure may be used to form an indicator tape. Such tapes may be prepared by coating and/or printing the water-based indicator composition on a substrate and drying the composition. If present, the binder may also be cured and/or crosslinked by, e.g., exposure to actinic radiation and/or heat. Suitable substrates are well-known and include paper, e.g., saturated paper. Generally, any of a variety of known coating and printing techniques may be used.

Examples

Materials used in the preparation of the following examples are summarized in Table 1.

TABLE 1

Materials and solubility information.

| | Solubility* | Supplier |
|---|---|---|
| Bi(III) compounds | | |
| bismuth citrate (org.) | slightly soluble | Alfa Aesar, Ward Hill, MA |
| bismuth subcarbonate (inorg.) | insoluble | Sigma-Aldrich, St. Louis, MO |
| bismuth subsalicylate (org.) | insoluble | Alfa Aesar |
| bismuth tartrate (org.) (sodium salt) | soluble | RSA Corp., Danbury, CT |
| bismuth oxide (inorg.) | insoluble | Sigma-Aldrich |
| Sulfur sources | | |
| sulfur | insoluble | Akrochem, Akron, OH |
| 1,3-diphenylthiourea | insoluble | Matheson, Norwood, OH |
| sodium thiosulfate | 76.4 g/100 ml | Sigma-Aldrich |
| tetramethylthiuram disulfide | insoluble | Sigma-Aldrich |
| Carbonate Salts | | |
| lithium carbonate | 1.3 g/100 ml | JT Baker, Phillipsburg, NJ |
| magnesium carbonate | 0.4 g/100 ml | MP Biomedicals, Solon, OH |
| sodium bicarbonate | 9.6 g/100 ml | Sigma-Aldrich |
| sodium carbonate | 21.6 g/100 ml | JT Baker |
| Resin | | |
| acrylic dispersion containing styrene and acrylonitrile | N/A | BASF Corporation, Charlotte, NC ("ACRONAL S 504") |
| Other | | |
| citric acid | 73 g/100 ml | Sigma-Aldrich |
| gallic acid | 1.2 g/100 ml | Mallinckrodt |
| oxalic acid | 9 g/100 ml | Sigma-Aldrich |
| trisodium citrate | 42.5 g/100 ml | VWR, Westchester, PA |
| sodium salicylate | 66 g/100 ml | Mallinckrodt, St. Louis, MO |

*Solubility data were compiled from a variety of sources.

Indicator formulations were prepared combining the components listed in Table 2 in a jar containing twenty 12.5 mm (0.5 inch) diameter ceramic marbles. The contents were mixed on a ball roller for sixteen hours.

TABLE 2

Sample compositions (amounts in grams).

| Component | EX-1 | EX-2 | EX-3 | EX-4 | EX-5 | EX-6 | CE-1 |
|---|---|---|---|---|---|---|---|
| bismuth subsalicylate | | | | | | 2.4 | |
| bismuth tartrate* | 2.4 | | | | | | |
| bismuth citrate | | 2.4 | 2.4 | 2.4 | 2.4 | | 16.8 |
| sulfur | 8.8 | 9.1 | 8.8 | 4.4 | 4.4 | 4.4 | |
| sodium thiosulfate | | | | | | | 7.2 |
| lithium carbonate | 11.2 | 11.2 | 5.6 | 11.2 | 5.6 | 5.6 | |
| sodium carbonate | | | | | | | 3.4 |
| ACRONAL S 504 | 24 | 24 | 24 | 24 | 24 | 24 | 20 |
| de-ionized water | 33.6 | 33.6 | 39.2 | 38.0 | 43.6 | 43.6 | 36.6 |
| total weight | 80.0 | 80.3 | 80.0 | 80.0 | 80.0 | 80.0 | 84.0 |

*sodium salt

Each of the formulations included an organic Bi(III) compound, a carbonate salt, and a sulfur source. In the formulation of comparative example CE-1, each of these components was water-soluble. The composition turned brown upon milling and was not used further. The formulations of Examples EX-1 through EX-6 included at least one water-insoluble component and each exhibited good shelf-life stability. None of the compositions exhibited darkening upon milling, or after two weeks storage at approximately 25° C.

The formulations of EX-1 through EX-6 were coated onto a backing using a #22 Meyer Rod and dried for thirty minutes at 45° C. The backing was a saturated 55 gram per square meter basis weight crepe paper with an acrylic top-coat, used to make 3M™ Masking Tape 2020. The coated backings were cut into approximately 0.64 cm (0.25 inch) by 3.8 cm (1.5 inch) strips. Samples from each example were treated for various times according to the following sterilization conditions:

1. steam in a JOSLYN resistometer at 121° C.;
2. steam in a JOSLYN resistometer at 134° C.;
3. steam in an AMSCO hospital steam sterilization vessel at 132° C.; and
4. dry heat in a dry oven at 140° C. for 30 minutes.

The optical density (OD) of each exposed sample was measured using a Macbeth RD917 densitometer using a white filter. Results are reported in Table 3. "ISO pass" and "ISO fail" designate the steam exposure test conditions for sterilization process indicators that are specified by the International Standards Organization in ISO11140.

TABLE 3

Optical density readings for Examples 1-6.

| Optical Density | EX-1 | EX-2 | EX-3 | EX-4 | EX-5 | EX-6 |
|---|---|---|---|---|---|---|
| Dry heat, 140° C., 30 min | 0.3 | 0.3 | 0.3 | 0.2 | 0.2 | 0.2 |
| Steam, 132° C., 4 min (hospital cycle) | 1.2 | 1.3 | 1.3 | 1.4 | 1.5 | 1.3 |
| Steam, 134° C., 2 min (ISO pass) | 1.1 | 1.2 | 1.2 | 1.4 | 1.3 | 0.7 |
| Steam, 134° C., 30 sec (ISO fail) | 0.6 | 0.3 | 0.3 | 0.4 | 0.3 | 0.2 |
| Steam, 121° C., 10 min (ISO pass) | 1.2 | 1.3 | 1.3 | 1.4 | 1.6 | 1.3 |
| Steam, 121° C., 3 min (ISO fail) | 1.0 | 0.8 | 0.8 | 1.0 | 1.0 | 0.2 |

While desired performance characteristics may vary by application, the inks were rated according to the criteria provided in Table 4. In particular, it is often desirable for an indicator to exhibit little or no color change (i.e., a low optical density value) upon exposure to dry heat while exhibiting a readily discernable color (i.e., a high optical density value) upon exposure to a typical hospital steam sterilization cycle. It may also be desirable for the color of an indicator to be significantly darker when exposed to conditions associated with effective sterilization (e.g., ISO pass at 134° C. or 121° C.) relative to comparable conditions associated with ineffective sterilization (e.g., ISO fail at 134° C. or 121° C.) as indicated by a difference in the optical density at pass conditions relative to fail conditions.

TABLE 4

Performance Criteria based on optical density values.

| Criteria | Conditions | A | B | C |
|---|---|---|---|---|
| Dry Heat | Dry heat, 140° C., 30 min | ≤0.3 | ≤0.5 | >0.5 |
| Hospital Cycle | Steam, 132° C., 4 min (hospital cycle) | ≥1.3 | ≥1.1 | <1.1 |
| ISO 134° C. | Steam, 134° C. (ISO pass-ISO fail) | ≥0.5 | ≥0.3 | <0.3 |
| ISO 121° C. | Steam, 121° C. (ISO pass-ISO fail) | ≥0.5 | ≥0.3 | <0.3 |
| Overall Grade | | A or B for all tests | A or B for both Dry Heat and Hospital Cycle | C for either Dry Heat or Hospital Cycle |

The qualitative performance of the various inks relative to these criteria is summarized in Table 5. The "Solubility" of the bismuth source, sulfur source, and the carbonate salt provided in Table 5 were assessed as follows. If material is known in the art as insoluble in water, Solubility is reported as "No." If the material is present in the ink in an amount below its solubility limit in water, Solubility is reported as "Yes." If the material is present in an amount greater than its solubility limit or if the available reported solubility was stated as slightly soluble, Solubility is reported as "slight." If more than one material from a particular category was present in the ink, the Solubility of each material is reported in Table 5.

TABLE 5

Summary of composition and performance of formulations EX-1 through EX-6.

| | | | Solubility | | | Performance | | | |
|---|---|---|---|---|---|---|---|---|---|
| Grade | EX. | Bi(III) | Bismuth Source | Sulfur Source | Carbonate Salt | Dry Heat | Hospital Cycle | ISO 134° C. | ISO 121° C. |
| A | 1 | Org | Yes | No | slight | A | B | A | C |
| A | 2 | Org | slight | No | slight | A | A | A | A |
| A | 3 | Org | slight | No | slight | A | A | A | A |
| A | 4 | Org | slight | No | slight | A | A | A | B |
| A | 5 | Org | slight | No | slight | A | A | A | A |
| A | 6 | Org | No | No | slight | A | A | A | A |

The ink compositions of Example EX-7 and Comparative Examples CE-2, CE-3, and CE-4 were prepared, coated, and evaluated according to the procedures described for Example 1 using the components summarized in Table 6a.

The optical density readings obtained upon exposure to various conditions are summarized in Table 6b and the performance ratings are shown in Table 6c.

TABLE 6a

Composition of Example EX-7 and Comparative Examples CE-2 through CE-4.

|  | Example | | | |
| --- | --- | --- | --- | --- |
|  | EX-7 | CE-2 | CE-3 | CE-4 |
| bismuth subcarbonate |  | 3.4 | 3.4 |  |
| bismuth subsalicylate | 2.4 |  |  |  |
| bismuth oxide |  |  |  | 3.1 |
| sulfur | 8.8 | 8.8 | 8.8 | 8.8 |
| lithium carbonate | 5.6 | 5.6 | 5.1 | 5.6 |
| sodium salicylate |  |  | 0.8 |  |
| ACRONOL S-504 | 24 | 24 | 24 | 24 |
| deionized water | 39.2 | 38.2 | 37.9 | 38.5 |
| Total Weight | 80 | 80 | 80 | 80 |

TABLE 6b

Optical density readings for EX-7 and CE-2 through CE-4.

|  | Example | | | |
| --- | --- | --- | --- | --- |
|  | EX-7 | CE-2 | CE-3 | CE-4 |
| Dry heat, 140° C., 30 min | 0.3 | 0.2 | 0.2 | 0.2 |
| Steam, 132° C., 4 min (hospital cycle) | 1.3 | 1.0 | 1.0 | 0.7 |
| Steam, 134° C., 2 min (ISO pass) | 1.0 | 0.8 | 0.9 | 0.4 |
| Steam, 134° C., 30 sec (ISO fail) | 0.4 | 0.4 | 0.4 | 0.4 |
| Steam, 121° C., 10 min (ISO pass) | 1.2 | 0.9 | 1.0 | 0.6 |
| Steam, 121° C., 3 min (ISO fail) | 0.7 | 0.6 | 0.8 | 0.4 |

TABLE 6c

Summary of formulations EX-7 and CE-2 through CE-4.

|  |  |  | Solubility | | | | Performance | | | |
| --- | --- | --- | --- | --- | --- | --- | --- | --- | --- | --- |
| Grade | EX. | Bi(III) | Bismuth Source | Sulfur Source | Carb. Salt | Other Cpt. | Dry Heat | Hospital Cycle | ISO 134° C. | ISO 121° C. |
| A | EX-7 | Org | No | No | slight | — | A | A | A | A |
| C | CE-2 | Inorg | No | No | slight | — | A | C | B | B |
| C | CE-3 | Inorg | No | No | slight | Yes* | A | C | A | C |
| C | CE-4 | Inorg | No | No | slight | — | A | C | C | C |

* sodium salicylate

The ink compositions of Example EX-7 and Comparative Examples CE-2 and CE-4 contained the same sulfur source and carbonate salt. However, Example EX-7 used an organic Bi(III) compound (bismuth subsalicylate) while the Bi(III) compounds of CE-2 (bismuth subcarbonate) and CE-4 (bismuth oxide) were inorganic.

X-ray diffraction analysis was used to determine the actual bismuth species present in the water-based ink compositions, according to the following Diffraction Procedure. The inks of Example EX-7 and Comparative Example CE-4 were each coated onto plate glass using a #22 Meyer Bar and dried in an oven for 30 minutes at 50° C. The dried ink was then removed from the plate glass by scraping with a razor blade and then submitted for x-ray diffraction analysis. The analysis for EX-7 showed bismuth subcarbonate as the only bismuth species. The analysis for CE-4 showed bismuth oxide as the only bismuth species.

The x-ray diffraction results demonstrate that the organic Bi(III) compound formed bismuth subcarbonate in situ upon reaction with the carbonate salt, yet EX-7 showed good performance. This is surprising, as the direct addition of sodium subcarbonate produced a poor indicating ink (CE-2).

One difference between the in situ formed composition of EX-7 and the composition of CE-2 is that EX-7 contained subsalicylate. Comparative Example CE-3 was prepared directly from bismuth subcarbonate, but included sodium salicylate in an attempt to mimic the presumed composition of EX-7 where the bismuth subcarbonate was prepared in situ. Despite comparable compositions, the performance of CE-3 was significantly worse than the performance of EX-7, demonstrating that the composition containing bismuth subcarbonate formed in situ differs in some respect from formulations prepared directly by the addition of bismuth subcarbonate.

The ink compositions of Example EX-8 through EX-11 were prepared, coated, and evaluated according to the procedures described for Example 1 using a variety of carbonate salts. Comparative Example CE-5 was similarly prepared; however, trisodium citrate was included rather than a carbonate salt. The compositions are summarized in Table 7a. The optical density readings obtained upon exposure to various conditions are summarized in Table 7b and the performance ratings are shown in Table 7c.

TABLE 7a

Composition of Examples EX-8 through EX-11 and CE-5.

|  | Example | | | | |
| --- | --- | --- | --- | --- | --- |
|  | EX-8 | EX-9 | EX-10 | EX-11 | CE-5 |
| bismuth subsalicylate | 2.4 | 2.4 | 2.4 | 2.4 | 2.4 |
| sulfur | 8.8 | 8.8 | 8.8 | 8.8 | 8.8 |
| lithium carbonate | 6.4 |  |  |  |  |
| sodium carbonate |  |  | 8 | 4 |  |
| sodium bicarbonate |  | 6.4 |  |  |  |
| trisodium citrate |  |  |  |  | 19.6 |

TABLE 7a-continued

Composition of Examples EX-8 through EX-11 and CE-5.

| | Example | | | | |
|---|---|---|---|---|---|
| | EX-8 | EX-9 | EX-10 | EX-11 | CE-5 |
| ACRONOL S-504 | 24 | 24 | 24 | 24 | 24 |
| deionized water | 38.4 | 38.4 | 36.8 | 40.8 | 25.2 |
| Total Weight | 80 | 80 | 80 | 80 | 80 |

TABLE 7b

Optical density readings for EX-8 through EX-11 and CE-5.

| | Example | | | | |
|---|---|---|---|---|---|
| | EX-8 | EX-9 | EX-10 | EX-11 | CE-5 |
| Dry heat, 140° C., 30 min | 0.2 | 0.4 | 0.4 | 0.4 | 0.3 |
| Steam, 132° C., 4 min (hospital cycle) | 1.3 | 1.4 | 1.4 | 1.4 | 0.7 |
| Steam, 134° C., 2 min (ISO pass) | 1.0 | 1.3 | 1.3 | 1.3 | 0.6 |
| Steam, 134° C., 30 sec (ISO fail) | 0.3 | 1.2 | 1.1 | 1.2 | 0.3 |
| Steam, 121° C., 10 min (ISO pass) | 1.3 | 1.3 | 1.3 | 1.4 | 1.0 |
| Steam, 121° C., 3 min (ISO fail) | 0.7 | 1.2 | 1.3 | 1.3 | 0.5 |

TABLE 7c

Summary of formulations EX-8 through EX-11 and CE-5.

| | | | Solubility | | | Performance | | | |
|---|---|---|---|---|---|---|---|---|---|
| Grade | EX. | Bi(III) | Bismuth Source | Sulfur Source | Carb. Salt | Other Cpt. | Dry Heat | Hospital Cycle | ISO 134° C. | ISO 121° C. |
| A | EX-8 | Org | No | No | slight | — | A | A | A | A |
| B | EX-9 | Org | No | No | Yes | — | B | A | C | C |
| B | EX-10 | Org | No | No | Yes | — | B | A | C | C |
| B | EX-11 | Org | No | No | Yes | — | B | A | C | C |
| C | CE-5 | Org | No | No | n/a | Yes* | A | C | B | C |

*Trisodium citrate

Each composition of Examples EX-8 through EX-11 contained the same insoluble bismuth source and sulfur source. The formulation of EX-8 included a slightly soluble carbonate salt, while each of EX-9 through EX-11 contained a soluble carbonate salt. All compositions performed well in the dry heat and hospital cycle tests and would be suitable as indicator inks. However, the examples containing soluble carbonate salts were inferior in the ISO 134° C. and ISO 121° C. tests. Comparative Example CE-5, which included trisodium citrate instead of a carbonate salt, produced a poor ink and demonstrates the importance of including a carbonate salt.

The ink compositions of Examples EX-12 through EX-17 were prepared, coated, and evaluated according to the procedures described for Example 1 with the addition of various additives. The compositions are summarized in Table 8a. The optical density readings obtained upon exposure to various conditions are summarized in Table 8b and the performance ratings are shown in Table 8c.

TABLE 8a

Composition of Examples EX-12 through EX-17.

| | Example | | | | | |
|---|---|---|---|---|---|---|
| | EX-12 | EX-13 | EX-14 | EX-15 | EX-16 | EX-17 |
| bismuth subsalicylate | 2.4 | 2.4 | 2.4 | 2.4 | 2.4 | 2.4 |
| sulfur | 8.8 | 8.8 | 8.8 | 8.8 | 8.8 | 8.8 |
| lithium carbonate | 5.6 | 4.4 | 4.3 | 5.6 | 5.6 | 5.6 |
| citric acid | 1.0 | | | | | 1.0 |
| trisodium citrate | | 1.3 | | | | |
| sodium salicylate | | | 0.8 | | | |
| gallic acid | | | | 1.0 | | |
| oxalic acid | | | | | 1.0 | |
| ACRONOL S-504 | 24 | 24 | 24 | 24 | 24 | 24 |
| deionized water | 38.2 | 39.1 | 39.7 | 38.2 | 38.2 | 38.2 |
| Total Weight | 80 | 80 | 80 | 80 | 80 | 80 |

TABLE 8b

Optical density readings Examples EX-12 through EX-17.

| | Example | | | | | |
|---|---|---|---|---|---|---|
| | EX-12 | EX-13 | EX-14 | EX-15 | EX-16 | EX-17 |
| Dry heat, 140° C., 30 min | 0.3 | 0.3 | 0.3 | 0.5 | 0.2 | 0.3 |
| Steam, 132° C., 4 min (hospital cycle) | 1.3 | 1.3 | 1.3 | 1.2 | 1.3 | 1.3 |
| Steam, 134° C., 2 min (ISO pass) | 1.2 | 1.3 | 1.0 | 1.3 | 1.0 | 1.3 |
| Steam, 134° C., 30 sec (ISO fail) | 0.6 | 1.0 | 0.4 | 0.8 | 0.3 | 0.5 |
| Steam, 121° C., 10 min (ISO pass) | 1.4 | 1.4 | 1.3 | 1.5 | 1.2 | 1.4 |
| Steam, 121° C., 3 min (ISO fail) | 1.1 | 1.4 | 0.7 | 1.4 | 0.7 | 1.2 |

TABLE 8c

Summary of formulations EX-12 through EX-17, each containing an insoluble organic Bi(III) source (bismuth subsalicylate), and insoluble sulfur source (sulfur), and a slightly soluble carbonate salt (lithium carbonate).

| | | additive | | Performance | | | |
|---|---|---|---|---|---|---|---|
| Grade | EX. | component | soluble | Dry Heat | Hospital Cycle | ISO 134° C. | ISO 121° C. |
| A | EX-12 | citric acid | Yes | A | A | A | B |
| B | EX-13 | trisodium citrate | Yes | A | A | B | C |
| A | EX-14 | sodium salicylate | Yes | A | A | A | A |
| B | EX-15 | gallic acid | Yes | B | B | A | A |
| B | EX-16 | oxalic acid | Yes | A | A | A | C |
| B | EX-17 | citric acid | Yes | A | A | A | C |

The ink compositions of Examples EX-18 through EX-23 and CE-6 were prepared, coated, and evaluated according to the procedures described for Example 1. A variety of sulfur sources and organic Bi(III) compounds were evaluated. The compositions are summarized in Table 9a. The optical density readings obtained upon exposure to various conditions are summarized in Table 9b and the performance ratings are shown in Table 9c.

TABLE 9a

Composition of CE-6 and EX-18 through EX-23.

| | Example | | | | | | |
|---|---|---|---|---|---|---|---|
| | CE-6 | EX-18 | EX-19 | EX-20 | EX-21 | EX-22 | EX-23 |
| bismuth subsalicylate | 2.4 | 2.4 | 2.4 | 2.4 | 2.4 | | |
| bismuth citrate | | | | | | 2.4 | 2.6 |
| sulfur | | | | 8.8 | 8.8 | 8.8 | 8.8 |
| tetramethyl-thiuramdisulfide | 8.3 | | | | | | |
| 1,3-diphenylthiourea | | 7.9 | | | | | |
| sodium thiosulfate | | | 5.4 | | | | |
| lithium carbonate | 5.6 | 5.6 | 5.6 | 5.6 | 5.6 | 5.6 | 5.6 |
| sodium carbonate | | | | | 1 | | |
| ACRONOL S-504 | 24 | 24 | 24 | 24 | 24 | 24 | 24 |
| deionized water | 39.7 | 40.1 | 42.6 | 39.2 | 38.2 | 39.2 | 39 |
| Total Weight | 80 | 80 | 80 | 80 | 80 | 80 | 80 |

TABLE 9b

Optical density readings for CE-6 and EX-18 through EX-23.

| | Example | | | | | | |
|---|---|---|---|---|---|---|---|
| | CE-6 | EX-18 | EX-19 | EX-20 | EX-21 | EX-22 | EX-23 |
| Dry heat, 140° C., 30 min | 0.3 | 0.2 | 0.2 | 0.2 | 0.4 | 0.3 | 0.3 |
| Steam, 132° C., 4 min (hospital cycle) | 0.2 | 1.3 | 1.2 | 1.2 | 1.3 | 1.3 | 1.4 |
| Steam, 134° C., 2 min (ISO pass) | 0.2 | 1.3 | 0.7 | 0.9 | 1.3 | 1.3 | 1.3 |
| Steam, 134° C., 30 sec (ISO fail) | 0.2 | 1.0 | 0.3 | 0.3 | 0.8 | 0.6 | 0.5 |
| Steam, 121° C., 10 min (ISO pass) | 0.3 | 1.3 | 1.2 | 1.3 | 1.3 | 1.4 | 1.4 |
| Steam, 121° C., 3 min (ISO fail) | 0.2 | 1.3 | 0.4 | 0.7 | 1.1 | 1.3 | 1.3 |

TABLE 9c

Summary of formulations CE-6 and EX-18 through EX-23.

| | | | Solubility | | | Performance | | |
| | | | Bismuth | Sulfur | Carbonate | Dry | Hospital | ISO | ISO |
| Grade | EX. | Bi(III) | Source | Source | Salt | Heat | Cycle | 134° C. | 121° C. |
|---|---|---|---|---|---|---|---|---|---|
| C | CE-6 | Org | No | No | slight | A | C | C | C |
| B | EX-18 | Org | No | No | slight | A | A | B | C |
| A | EX-19 | Org | No | Yes | slight | A | B | A | A |
| A | EX-20 | Org | No | No | slight | A | B | A | A |
| B | EX-21 | Org | No | No | slight + Yes | B | A | A | C |
| B | EX-22 | Org | slight | No | slight | A | A | A | C |
| B | EX-23 | Org | slight | No | slight | A | A | A | C |

The ink of EX-22 was prepared from an organic Bi(III) compound. This ink was evaluated according to the Diffraction Procedure. Similar to the inks prepared from bismuth subsalicylate, the x-ray diffraction results showed bismuth subcarbonate as the only bismuth species. Again, the formation of bismuth subcarbonate in situ from the reaction of an organic Bi(III) compound with a carbonate salt resulted in an effective indicating ink (Examples EX-22 and EX-23). In contrast, inks prepared directly from bismuth subcarbonate were poor.

Certain organic Bi(III) compounds and carbonate salts have been exemplified. However, numerous other combinations will be apparent to one of ordinary skill in the art. In addition, upon reviewing the present application, one of ordinary skill in the art could make such selections applying nothing more than routine experimentation. For example, the present inventors have discovered that the Diffraction Procedure may be used to screen potential combinations of organic Bi(III) compounds and carbonate salts.

Bismuth oxide and lithium carbonate. To 1 gram bismuth oxide in 40 ml water was added 5 grams lithium carbonate with stirring. The resulting slurry was allowed to stand at room temperature for 30 minutes and then filtered using Whatman filter paper. The filtrate was dried at room temperature over 48 hours and then subjected to x-ray diffraction analysis, which showed the presence of bismuth oxide as the only bismuth species.

Bismuth subsalicylate and lithium carbonate. To 1 gram bismuth subsalicylate in 40 ml water was added 2 g lithium carbonate with stirring. The mixture was heated to boiling with stirring. The resulting slurry was allowed to stand at room temperature for 30 minutes and then filtered using Whatman filter paper. The filtrate was dried at room temperature over 48 hours and then subjected to x-ray diffraction analysis, which showed the presence of bismuth subcarbonate as the only bismuth species.

Bismuth citrate and lithium carbonate. To 1 gram bismuth citrate in 40 ml water was added 2 g lithium carbonate with stirring. The mixture was heated to 40° C. with stirring. The resulting slurry was allowed to stand at room temperature for 30 minutes and then filtered using Whatman filter paper. The filtrate was dried at room temperature over 48 hours and then subjected to x-ray diffraction analysis, which showed the presence of bismuth subcarbonate as the only bismuth species.

Generally, a variety of known additives may be included in various formulations of the present disclosure. For example, surfactants and rheology modifiers can be added to suspend the insoluble components of the formulation as well as to improve print quality of the ink formulations. Dyes may be included to adjust the ultimate color achieved upon exposure to specific sterilization conditions. For example, in some embodiments, a dye may be included to shift the color from dark brown to black.

Various other modifications and alterations of this invention will become apparent to those skilled in the art without departing from the scope and spirit of this invention.

What is claimed is:

1. An indicator formulation comprising an indicating composition dispersed in water, wherein the indicating composition comprises
   (a) an organic Bi(III) compound;
   (b) elemental sulfur; and
   (c) lithium carbonate;
wherein the organic Bi(III) compound has a solubility in water at 20° C. of less than 5 grams/100 ml.

2. The indicator formulation of claim 1, wherein the indicating composition comprises bismuth subcarbonate formed in situ.

3. The indicator formulation of claim 1, wherein the organic Bi(III) compound has a solubility in water at 20° C. of less than 1 gram/100 ml.

4. The indicator formulation of claim 1 wherein the organic Bi(III) is selected from the group consisting of bismuth subsalicylate, bismuth citrate, bismuth tartrate, and combinations thereof.

5. The indicator formulation of claim 1, further comprising an acidic compound.

6. The indicator formulation of claim 5, wherein the acidic compound is non-polymeric.

7. The indicator formulation of claim 6, wherein the acidic compound is selected from the group consisting of citric acid, gallic acid, oxalic acid, and combinations thereof.

8. The indicator formulation of claim 1, further comprising a resin.

9. The indicator formulation of claim 8, wherein the resin comprises an acrylic resin.

10. An indicator tape comprising a substrate and an indicator composition on a portion of at least one surface of the substrate, wherein the indicator tape was prepared by the process of applying the indicator formulation according to any one of the preceding claims to the surface of the substrate and drying the formulation.

11. A method of preparing an indicator formulation comprising combining an organic Bi(III) compound; elemental sulfur; and lithium carbonate in water; wherein the organic Bi(III) compound has a solubility in water at 20° C. of less than 5 grams/100 ml, and reacting the organic Bi(III) compound with the lithium carbonate to form bismuth subcarbonate.

* * * * *

UNITED STATES PATENT AND TRADEMARK OFFICE
CERTIFICATE OF CORRECTION

PATENT NO. : 9,588,052 B2
APPLICATION NO. : 14/366731
DATED : March 7, 2017
INVENTOR(S) : Kevin D. Landgrebe et al.

Page 1 of 1

It is certified that error appears in the above-identified patent and that said Letters Patent is hereby corrected as shown below:

On the Title Page

Item (56) References Cited under OTHER PUBLICATIONS, Line 1, "Bismuthi" should read --Bismuth--.

In the Claims

Column 16,
Line 47, "claim 1" should read --claim 1,--.

Column 17,
Line 1, "any one of the preceding claims" should read --claim 1--.

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*